(12) United States Patent
Zhuang

(10) Patent No.: US 12,310,705 B2
(45) Date of Patent: May 27, 2025

(54) CARDIAC PHYSIOLOGICAL PARAMETER ACQUISITION DEVICE

(71) Applicant: SHENZHEN DARMA TECHNOLOGY CO., LTD., Shenzhen (CN)

(72) Inventor: Shaochun Zhuang, Shenzhen (CN)

(73) Assignee: CARDIOSTORY INC., Lewes, DE (US)

( * ) Notice: Subject to any disclaimer, the term of this patent is extended or adjusted under 35 U.S.C. 154(b) by 169 days.

(21) Appl. No.: 18/084,527

(22) Filed: Dec. 19, 2022

(65) Prior Publication Data

US 2023/0190123 A1     Jun. 22, 2023

(30) Foreign Application Priority Data

Dec. 20, 2021 (CN) .......................... 202123210601.X

(51) Int. Cl.
*A61B 5/024* (2006.01)
*A47G 9/10* (2006.01)
*A61B 5/00* (2006.01)

(52) U.S. Cl.
CPC ........ *A61B 5/02427* (2013.01); *A47G 9/1009* (2013.01); *A47G 9/1081* (2013.01); *A61B 5/6892* (2013.01)

(58) Field of Classification Search
CPC ....... A61B 5/6822; A61B 5/6823; A61B 6/04; A61B 6/0407
See application file for complete search history.

(56) References Cited

U.S. PATENT DOCUMENTS

| | | | | |
|---|---|---|---|---|
| 5,438,719 A | * | 8/1995 | Anthony ................... | A47G 9/02 5/490 |
| 5,813,065 A | * | 9/1998 | Tinhorn .................... | A47G 9/10 5/639 |
| 6,123,389 A | * | 9/2000 | O'Connor ............ | B60N 2/2851 5/636 |
| 6,381,784 B1 | * | 5/2002 | Davis ....................... | A61G 7/07 5/636 |
| 9,586,021 B2 | * | 3/2017 | Franceschetti ........... | A61B 5/01 |
| 9,836,942 B2 | * | 12/2017 | Wiggermann ....... | A61B 5/1071 |
| 9,848,712 B2 | * | 12/2017 | Main ...................... | A47C 31/12 |
| 9,931,085 B2 | * | 4/2018 | Young ................... | A61B 5/1117 |
| 9,981,107 B2 | * | 5/2018 | Franceschetti ....... | A61B 5/0816 |

(Continued)

*Primary Examiner* — Oommen Jacob
(74) *Attorney, Agent, or Firm* — Cheng-Ju Chiang

(57) ABSTRACT

The present invention provides an information acquisition device, comprising: a cushion for supporting a subject to be tested; a neck pillow for the subject to be tested to place his neck thereon; a fiber-optic sensor group for obtaining physical signs of the subject to be tested; and a signal acquisition module connected to the fiber-optic sensor group; wherein the signal acquisition module is wrapped in the neck pillow, the fiber-optic sensor group is placed in the cushion, and the neck pillow is connected with the cushion. In the present invention, by setting a neck pillow connected with the cushion so that the subject can adjust the body position independently without assistance to a preferred measurement position, and can complete information acquisition by himself. In addition, the signal acquisition module is placed in the neck pillow, so that the structure of the information acquisition device is more concise.

9 Claims, 2 Drawing Sheets

(56) References Cited

U.S. PATENT DOCUMENTS

| | | | |
|---|---|---|---|
| 10,238,560 B2* | 3/2019 | O'Keefe | A61H 9/0078 |
| 10,278,512 B2* | 5/2019 | Stjerna | A47C 27/061 |
| 10,820,728 B1* | 11/2020 | Rao | A47G 9/10 |
| 10,905,249 B1* | 2/2021 | Saghiri | A61B 5/6892 |
| 11,241,100 B2* | 2/2022 | Chapin | A47C 21/044 |
| 11,424,646 B2* | 8/2022 | Holmvik | H02J 50/12 |
| 11,439,345 B2* | 9/2022 | Young | A61B 5/725 |
| 11,712,384 B2* | 8/2023 | Stusynski | A61G 7/018 |
| | | | 5/613 |
| 2004/0177449 A1* | 9/2004 | Wong | A47C 27/083 |
| | | | 5/713 |
| 2011/0068928 A1* | 3/2011 | Riley | A61B 5/024 |
| | | | 340/573.1 |
| 2011/0224510 A1* | 9/2011 | Oakhill | A61B 5/4815 |
| | | | 600/301 |
| 2011/0295083 A1* | 12/2011 | Doelling | A61B 5/11 |
| | | | 600/407 |
| 2013/0245389 A1* | 9/2013 | Schultz | A61B 5/68 |
| | | | 600/301 |
| 2013/0317399 A1* | 11/2013 | Ribble | G16H 20/30 |
| | | | 601/84 |
| 2015/0230635 A1* | 8/2015 | Abrams | A47G 9/1081 |
| | | | 5/636 |
| 2016/0015183 A1* | 1/2016 | Stjerna | A47C 27/082 |
| | | | 5/690 |
| 2016/0302596 A1* | 10/2016 | Ross | A47C 27/086 |
| 2016/0324431 A1* | 11/2016 | Ng | A61B 5/11 |
| 2017/0173297 A1* | 6/2017 | Park | A61M 21/00 |
| 2017/0296103 A1* | 10/2017 | Ojha | A47G 9/1045 |
| 2018/0256911 A1* | 9/2018 | Funane | A61H 23/00 |
| 2019/0110617 A1* | 4/2019 | Berney | A47G 9/0253 |
| 2019/0110618 A1* | 4/2019 | Ye | A47C 7/383 |
| 2020/0405193 A1* | 12/2020 | Hu | A61B 5/1116 |
| 2020/0405526 A1* | 12/2020 | Yu | A61B 5/4836 |
| 2022/0248883 A1* | 8/2022 | Williams | A47G 9/1054 |
| 2023/0190123 A1* | 6/2023 | Zhuang | A61B 5/1102 |
| | | | 600/479 |

* cited by examiner

CARDIAC PHYSIOLOGICAL PARAMETER ACQUISITION DEVICE

CROSS REFERENCE TO RELATED APPLICATIONS

The present invention is a 35 U.S.C. § 119 benefit of earlier filing date; right of priority of Chinese Application No. 202123210601.X, filed on Dec. 20, 2021, the disclosure of which is incorporated by reference herein.

BACKGROUND OF THE INVENTION

Field of the Invention

The present invention relates to the field of signal acquisition, and more particularly, to a cardiac physiological parameter acquisition device.

Description of Related Art

The heart is an important organ of the human body. For heart failure patients, effective heart monitoring is of great significance for heart failure management. At present, invasive monitoring devices in heart monitoring are too expensive to be accepted by patients for only monitoring needs, non-invasive monitoring devices have the advantages of operation and human friendliness. For example, devices used to monitor mechanical motion of the heart, the signal quality of cardiac monitoring signals acquired by which are closely related to the placement position of the device, and the device often requires someone else, such as a caregiver, to help the patient calibrate the position. Therefore, there is a need for an information acquisition device with a position-assisted self-determination function.

BRIEF SUMMARY OF THE INVENTION

An object of the present invention is to provide an information acquisition device, which aims to solve the problem of existing heart monitoring devices that require others to help patients calibrate the position.

The present invention provides an information acquisition device, comprising: a cushion for supporting a subject to be tested; a neck pillow for the subject to be tested to place his neck thereon; a fiber-optic sensor group for obtaining physical signs of the subject to be tested; and a signal acquisition module connected to the fiber-optic sensor group; wherein the signal acquisition module is wrapped in the neck pillow, the fiber-optic sensor group is placed in the cushion, and the neck pillow is connected with the cushion.

In accordance some embodiment, the neck pillow comprises a top cover and a base; the top cover and the base are connected, wrap the signal acquisition module in the neck pillow, and wrap a side edge of the cushion.

In accordance some embodiment, the top cover and the base are connected through screws/holes, or columns/openings, or convex/concave, a snap fit or a tension fit.

In accordance some embodiment, the top cover of the neck pillow is U-shaped, including a left protrusion, a flat pillow part and a right protrusion, and a front height of the neck pillow is greater than a rear height.

In accordance some embodiment, the flat pillow part of the neck pillow is placed at a middle of the side edge of the cushion, a bottom length of the flat pillow part is any value between 7 cm and 13 cm, and a top opening length of the flat pillow part is any value between 11 cm and 16 cm.

In accordance some embodiment, the neck pillow is made of hard materials; an outer surface of neck pillow is covered with a flexible layer made of flexible materials.

In accordance some embodiment, the fiber-optic sensor group comprises a left sensor, a right sensor, a middle sensor, a first sensor and a second sensor; the left sensor corresponds to a left shoulder region of the subject to be tested; the right sensor corresponds to a right shoulder region of the subject to be tested; the middle sensor corresponds to a middle shoulder region of the subject to be tested, the first sensor correspond to a waist region of the subject to be tested, and the second sensor correspond to the waist region of the subject to be tested.

In accordance some embodiment, a length of the left sensor or the right sensor is any value between 10 cm and 20 cm, a length of the middle sensor is any value between 7 cm and 15 cm; a width of the left sensor, the right sensor, or the middle sensor is any value between 20 cm and 30 cm; a length of the first sensor or the second sensor is any value between 40 cm and 50 cm, and a width of the first sensor or the second sensor is any value between 5 cm and 10 cm.

In accordance some embodiment, the left sensor, middle sensor and right sensor are arranged side by side in an upper part of the cushion, where an upper side edge of the cushion is connected to the neck pillow.

In accordance some embodiment, the first sensor corresponding to the waist of the body is placed in a middle part of the cushion behind the left sensor, the middle sensor, and the right sensor side by side in the upper part of the cushion; the second sensor corresponding to the waist of the body is placed in a lower part of the cushion after the first sensor.

In accordance some embodiment, the flat pillow part for supporting the neck of the subject to be tested is adapted for the physiological curvature of the human cervical spine, whereby the subject to be tested can adjust the body position independently without assistance to a position without discomfort to obtain a preferred measurement position.

In the present invention, by setting a neck pillow connected with the cushion of the information acquisition device so that the subject to be tested can adjust the body position by himself without assistance to a preferred measurement position, and the subject to be tested can complete information acquisition by himself. In addition, the signal acquisition module is placed in the neck pillow to effectively use an internal space of the neck pillow, so that the structure of the information acquisition device is more concise.

DETAILED DESCRIPTION OF THE INVENTION

In order to make the subject, technical solutions, and advantages of the present invention clearer, the present invention will be described in further detail below with reference to the accompanying drawings and embodiments. The embodiments described herein are only used to explain the present invention, but not to limit the present invention.

The following embodiments illustrate the technical solutions.

Figure 1:
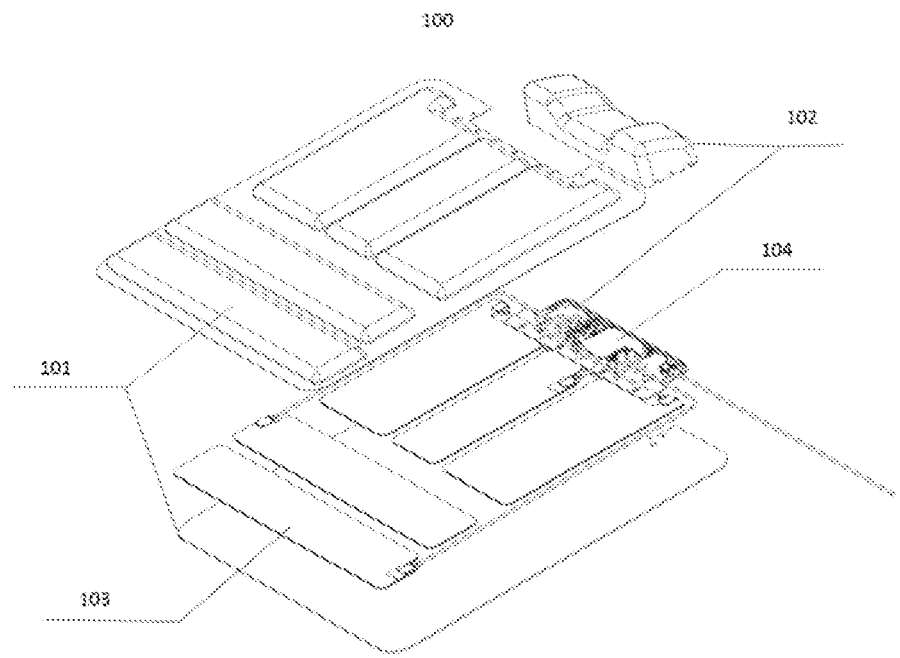
FIG. 1 is an exploded view of an information acquisition device in accordance with an embodiment of the present invention.

Referring to FIG. 1, an information acquisition device 100, which is used to acquire physical signs of a human body. The subject needs to lie supine on it to acquire physical signs. The information acquisition device 100 includes a cushion 101, a neck pillow 102, a fiber-optic sensor group 103, and a signal acquisition module 104.

The cushion 101 is used to support the subject to be tested, and the subject to be tested can lie on his back or leaning on it. The cushion 101 includes a top surface and a bottom surface, and the shape of the outer surfaces can be rectangular, square, or circular or other shape. The neck pillow 102 is used for the subject to be tested to place the neck when lying on his back. and the fiber-optic sensor group 103 is used to obtain physical signs of the subject to be tested, and is wrapped in the cushion 101. The fiber-optic sensor group 103 is connected to the signal acquisition module 104, the signal acquisition module 104 is wrapped in the neck pillow 102, the neck pillow 102 is connected to the cushion 101, and the neck pillow 102 can be placed at one side edge of the cushion 101, and preferably at a middle of the side edge.

Figure 2:
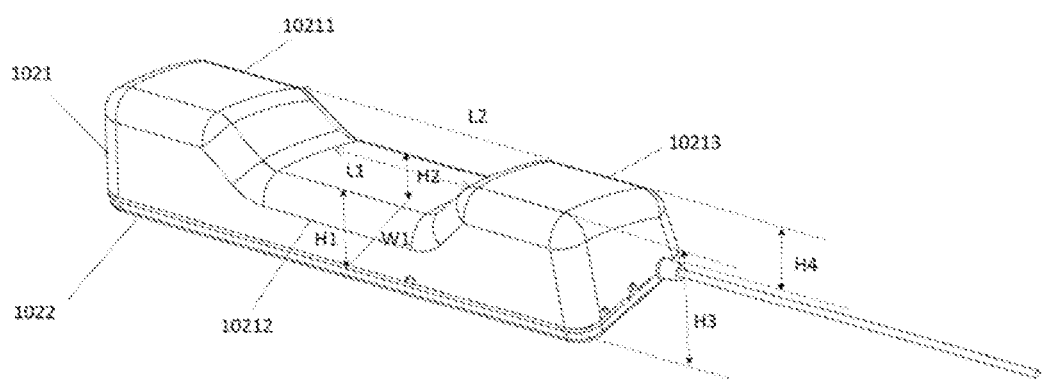
FIG. 2 is a perspective view of a neck pillow in accordance with the embodiment of the present invention.

Referring to FIG. 2, the neck pillow 102 includes a top cover 1021 and a base 1022. The top cover 1021 or the neck pillow 102 may be configured in a U-shape, including a left protrusion 10211 (namely, a left part of the U-shaped neck pillow 102), a flat pillow part 10212 (namely, a middle bottom of the U-shaped neck pillow 102) and a right protrusion 10213 (namely, a right part of the U-shaped neck pillow 102). The left protrusion 10211, flat pillow part 10212 and right protrusion 10213 can be an integral structure or an inseparable structure. A bottom length L1 of the flat pillow part 10212 is any value between 7 cm and 13 cm, such as 10 cm. A top opening length L2 of the U-shaped neck pillow 102 or the flat pillow part 10212, is any value between 11 cm and 16 cm such as 13.5 cm. A front height of the flat pillow part 10212 (namely the middle bottom of the U-shaped neck pillow 102) is greater than a rear height thereof the front height H1 is any value between 15 mm and 25 mm, such as 20 mm; and the rear height H2 is any value between 5 mm and 15 mm, such as 10 mm. Herein, the front height refers to the height of the side of the flat pillow part 10212 close to the cushion 101 and in contact with the shoulder of the subject to be tested. A width W1 of the neck pillow 102 or the flat pillow part 10212 is any value between 70 mm and 90 mm, such as 80 mm. The flat pillow part 10212 is a concave cavity of the whole neck pillow 102, which has a dimension to conforms to the physiological curvature of the human cervical spine and to adapt to different subjects of different body shapes; and provide a space for the subject to adjust the neck. The subject to be tested lies supine on the cushion 101 when performing sign acquisition, and his neck is placed on the flat pat 10212 of the neck pillow 102. Since there is a height difference between the front height and the rear height, the flat pillow part 10212 can support the neck and is adapted for the physiological curvature of the human cervical spine, so that the subject to be tested is more comfortable when lying down. When the subject places the neck on the flat pillow part 10212 and he doesn't feel uncomfortable, the subject to be tested is in a favorable (or preferred) test position at this time. If the subject to be tested feels uncomfortable, can adjust his body position by himself for a favorable position until the discomfort disappears. The left protrusion 10211 and the right protrusion 10213 are located at the left and right ends of the flat pillow part 10212. A front height H3 of the left protrusion 10211 and the right protrusion 10123 is greater than a rear height H4 thereof. The front height H3 can be any value between 40 mm and 60 mm, such as 50 mm, the rear height H4 can be any value between 30 mm and 40 mm, such as 35 mm. The flat pillow part 10212, the left protrusion 10211 and the right protrusion 10213 together construct the neck pillow 102 for the user to place his neck, and define a space for the subject to be tested to adjust his body position, that define a space range of a favorable test position to adapt to different subjects with different physical conditions.

Figure 3:
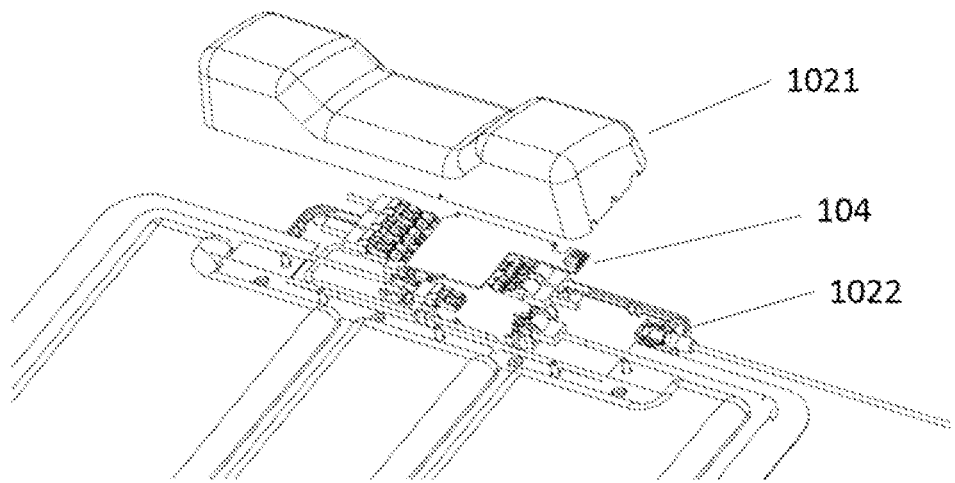
FIG. 3 is a partly exploded view of the information acquisition device in accordance with the embodiment of the present invention.

Referring to FIG. 3, the signal acquisition module 104 can be placed in the base 1022 of the neck pillow 102. The base 1022 has a plurality of columns, and a plurality of openings spaced apart from each other are defined in one side edge of the cushion 101, the columns of the base 1022 are inserted through or in the opening of the cushion 101, so that the base 1022 is connected with the cushion 101. The top cover 1021 and the base 1022 may be connected by threads, and the signal acquisition module 104 and part of the side edge of the cushion 101 are wrapped in the neck pillow 102. The neck pillow may also have the same size as the side edge of the cushion, so as to completely wrap the side edge of the cushion inside. In other embodiments, the top cover and the base of the neck pillow 102 can also adopt other structures, for example, the neck pillow 102 is connected with the cushion 101 by means of buckle connection, etc. The signal acquisition module 104 is connected with each fiber-optic sensor of the fiber-optic sensor group 103 to perform signal acquisition, and may also have an output interface for external data output lines, or have a wireless output interface, through Wi-Fi, Bluetooth, infrared or in other ways to output data. The signal acquisition module 104 may also perform signal processing.

The neck pillow 102 can be made of hard material, such as hard plastic material, such as ABS+PC materials, which can provide protection for the signal acquisition module 104. The neck pillow 102 may be designed ergonomically so that the subject can adjust the body position by himself, and adjust to a more comfortable state to obtain a preferred test position. The outer surface of the neck pillow 102 may have a protective layer or cover, for example, is covered with a layer of flexible material, such as silicone, which is more comfortable when the human body touches it, so that the subject to be tested feels more comfortable when his body rests on the neck pillow.

Figure 4:
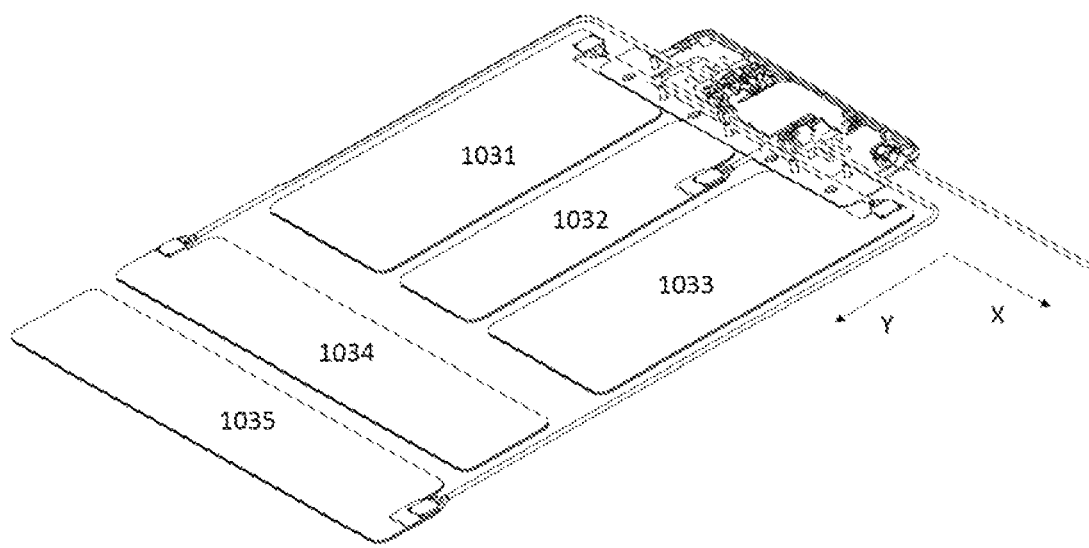
FIG. 4 is a perspective view of the information acquisition device without a top cover of the neck pillow in accordance with an embodiment of the present invention.

Referring to FIG. 4, the fiber-optic sensor group 103 includes a left sensor 1031 corresponding to the left shoulder of the body, a middle sensor 1032 corresponding to the middle shoulder of the body, a right sensor 1033 corresponding to the right shoulder of the body, a first sensor 1034 and a second sensor 1035 both corresponding to the waist of the body. When the subject to be tested lies supine on the cushion 101, the left sensor 1031 corresponds to the left shoulder region of the subject to be tested, the right sensor 1033 corresponds to the right shoulder region of the subject to be tested, and the middle sensor 1032 corresponds to the region between the left shoulder and the right shoulder of the subject (referred to as the middle shoulder). The left sensor 1031, middle sensor 1032 and right sensor 1033 are arranged side by side in an upper part of the cushion 101, where an edge (namely the upper side edge) of the cushion 101 is connected to the neck pillow 102, and the neck pillow 102 is located at the middle of the connected edge of the cushion 101.

Take the extending direction of the edge of the cushion 101 where the neck pillow 102 is located as the X-axis, and the Y-axis in a direction perpendicular to the X-axis. When describing the size of the sensors, the length along the X-axis is defined, and the width along the Y-axis is defined. A length of the left sensor 1031 corresponding to the left shoulder of the body can be any value between 10 cm to 20 cm such as 15 cm, a width of the left sensor 1031 can be any value between 20 cm to 30 cm such as 25 cm, and the right sensor 1033 may be similar as the left sensor 1031 in dimensions. A length of the middle sensor 1032 can be any value between 7 cm and 15 cm, such as 10 cm, and a width of the middle sensor 1032 can be any value between 20 cm and 30 cm, such as 23 cm. The left sensor 1031 and the right sensor 1033 are symmetrically distributed along the central axis of the middle sensor 1032 in the Y-axis direction. A length of the first sensor 1034 corresponding to the waist of the body can be any value between 40 cm and 50 cm, such as 45 cm, and a width of the first sensor 1034 can be any value between 5 cm and 10 cm, such as 7.5 cm. The second sensor 1035 corresponding to the waist of the body may have similar dimensions as the first sensor 1034 corresponding to the waist of the body. The first sensor 1034 corresponding to the waist of the body is placed in a middle part of the cushion 101 behind the left sensor 1031, middle sensor 1032 and the right sensor 1033 side by side in the upper part of the cushion 101. The second sensor 1035 corresponding to the waist of the body is placed in a lower part of the cushion 101 after the first sensor 1034. When the subject to be tested is lying on the cushion 101, the first sensor 1034 and the second sensor 1035 correspond to the waist of the subject.

In the present invention, by setting a neck pillow connected with the cushion of the information acquisition device so that the subject to be tested can adjust the body position by himself to a preferred measurement position without help, and the subject to be tested can complete information acquisition by himself, In addition, the signal acquisition module is placed in the neck pillow to effectively use an internal space of the neck pillow, so that the structure of the information acquisition device is more concise.

The technical features of the above embodiments can be combined arbitrarily. In order to make the description simple, all possible combinations of the technical features in the above embodiments are not described. However, as long as there is no contradiction in the combination of these technical features It is considered to be the range described in this specification.

The above examples only represent several embodiments of the present invention, and the descriptions thereof are specific and detailed, but should not be construed as a limitation on the scope of the invention patent. It should be pointed out that for those of ordinary skill in the art, without departing from the concept of the present invention, several modifications and improvements can also be made, which all belong to the protection scope of the present invention. Therefore, the protection scope of the patent of the present invention should be subject to the appended claims.

What is claimed is:

1. A cardiac physiological parameter acquisition device, comprising:
   a cushion, used for a subject to be tested lying supine thereon, having a plane shape defined as an XY plane and comprising an upper part, a middle part and lower part in a Y-axis direction;
   a neck pillow, being made of hard materials, U-shaped and connected to the upper part of the cushion; wherein the neck pillow comprises:
   a left protrusion;
   a right protrusion; and
   a flat pillow part formed by means of a concave cavity between the left protrusion and a right protrusion, which is used to support the neck of the subject lying supine on the cushion;
   a fiber-optic sensor group, used for obtaining physical signs of the subject, placed in the cushion, and comprising a left sensor, a right sensor, a middle sensor, a first sensor placed in the middle part of the cushion, and a second sensor placed in the lower part of the cushion; wherein the left sensor, the middle sensor and the right sensor are arranged side by side along an X-axis direction and located in the upper part of the cushion; the first sensor and the second sensor are parallel to each other and extend in the X-axis direction at an end of the left sensor, the middle sensor and the right sensor, and each of the first sensor and the second sensor has a length greater than a total length of the left sensor, the middle sensor and the right sensor in the X-axis direction; and
   a signal acquisition module used for performing signal acquisition, being wrapped in the neck pillow and connected to the fiber-optic sensor group;
   wherein the flat pillow part has a dimension conforming to a physiological curvature of the human cervical spine and adapted to different subjects with different physical conditions, the dimension comprises a bottom length L1 of 7-13 cm in the X-axis direction, a top opening length L2 of 11-16 cm in the X-axis direction, a front height H1 of 15-25 mm, a rear height H2 of 5-15 mm, and a width W1 of 70-90 mm in the Y-axis direction; the flat pillow part provides a space for the subject to adjust his neck and accordingly adjust his body position by himself to a preferred measurement position on the cushion; at the preferred measurement position, the subject feels comfortable, the left sensor corresponds to the left shoulder region of the subject, the right sensor corresponds to the right shoulder region of the subject, the middle sensor corresponds to the middle shoulder region of the subject, the first sensor and the second sensor correspond to a waist region of the subject, whereby the subject can adjust the body position independently without assistance to a position without discomfort to obtain the preferred measurement position.

2. The device as claimed in claim 1, wherein the neck pillow comprises a top cover and a base; the top cover and the base are connected, wrap the signal acquisition module in the neck pillow, and wrap a side edge of the cushion.

3. The device as claimed in claim 2, wherein the top cover and the base are connected through screws/holes, or columns/openings, or convex/concave, a snap fit or a tension fit.

4. The device as claimed in claim 2, wherein the top cover of the neck pillow is U-shaped, including a left protrusion, a flat pillow part and a right protrusion, and a front height of the neck pillow is greater than a rear height.

5. The device as claimed in claim 4, wherein the flat pillow part of the neck pillow is placed at a middle of the side edge of the cushion.

6. The device as claimed in claim 1, wherein a length of the left sensor or the right sensor is any value between 10 cm and 20 cm, a length of the middle sensor is any value between 7 cm and 15 cm; a width of the left sensor, the right sensor, or the middle sensor is any value between 20 cm and 30 cm; a length of the first sensor or the second sensor is any value between 40 cm and 50 cm, and a width of the first sensor or the second sensor is any value between 5 cm and 10 cm.

7. The device as claimed in claim 1, wherein an upper side edge of the cushion is connected to the neck pillow.

8. The device as claimed in claim 1, wherein the signal acquisition module has an output interface for connecting an external data output line, or has a wireless output interface to output data through Wi-Fi, Bluetooth, or infrared communication.

9. The device as claimed in claim 1, wherein the signal acquisition module is used to perform signal processing.

* * * * *